United States Patent [19]

Csongor et al.

[11] Patent Number: 6,074,578
[45] Date of Patent: Jun. 13, 2000

[54] BARREL WALL CONDUIT ARRANGEMENTS FOR A PLASTIC PROCESSING SCREW MACHINE

[76] Inventors: Desider G. Csongor, 19 Bennett St.; Donald N. Halgren, 35 Central St., both of Manchester, Mass. 01944

[21] Appl. No.: 08/773,920

[22] Filed: Dec. 30, 1996

Related U.S. Application Data

[63] Continuation-in-part of application No. 08/511,055, Aug. 3, 1995, Pat. No. 5,670,112, and a continuation-in-part of application No. 08/393,200, Feb. 23, 1995, abandoned.

[51] Int. Cl.[7] ........................................................ B29B 7/42
[52] U.S. Cl. ........................ 264/1.29; 264/1.28; 264/45.1; 264/171.13; 264/171.14; 264/172.15; 264/173.16; 264/211; 264/211.21; 264/328.17; 264/328.18; 264/572; 264/573; 425/113; 425/130; 425/133.1; 425/207
[58] Field of Search ........................ 264/572, 50, 328.17, 264/328.18, 1.29, 1.28, 45.1, 45.9, 573, 171.13, 171.14, 211, 211.13, 211.21, 172.15, 173.16; 425/133.1, 207, 130, 113

[56] References Cited

U.S. PATENT DOCUMENTS

| | | | |
|---|---|---|---|
| 3,782,870 | 1/1974 | Schippers | 425/133.1 |
| 4,467,969 | 8/1984 | Godfrey et al. | 264/37 |
| 4,548,776 | 10/1985 | Holdredge, Jr. | 264/50 |
| 4,730,935 | 3/1988 | Kolossow | 425/207 |
| 4,774,047 | 9/1988 | Nakamura et al. | 264/513 |
| 4,783,292 | 11/1988 | Rogers | 264/50 |

*Primary Examiner*—Catherine Timm
*Attorney, Agent, or Firm*—D. N. Halgren

[57] ABSTRACT

The invention comprises a plasticating machine for the working and forcing of plastic material into a mold, the machine including an elongated barrel housing having a first or proximal end and a second or distal end, and an elongated screw shaft with a screw flight therearound, the screw shaft being rotatably supported in the elongated barrel housing, for the working of plastic between the screw shaft and the elongated housing. At least one delivery conduit is generally longitudinally arranged within the wall of the housing. The delivery conduit with the housing wall may be arranged to heat or cool the screw and any plastic being worked therethrough. In a further embodiment, it may permit delivery of a medium within the wall, from an upstream location of the housing, into the primary flow path of any plastic being driven from the machine and into a mold.

3 Claims, 2 Drawing Sheets

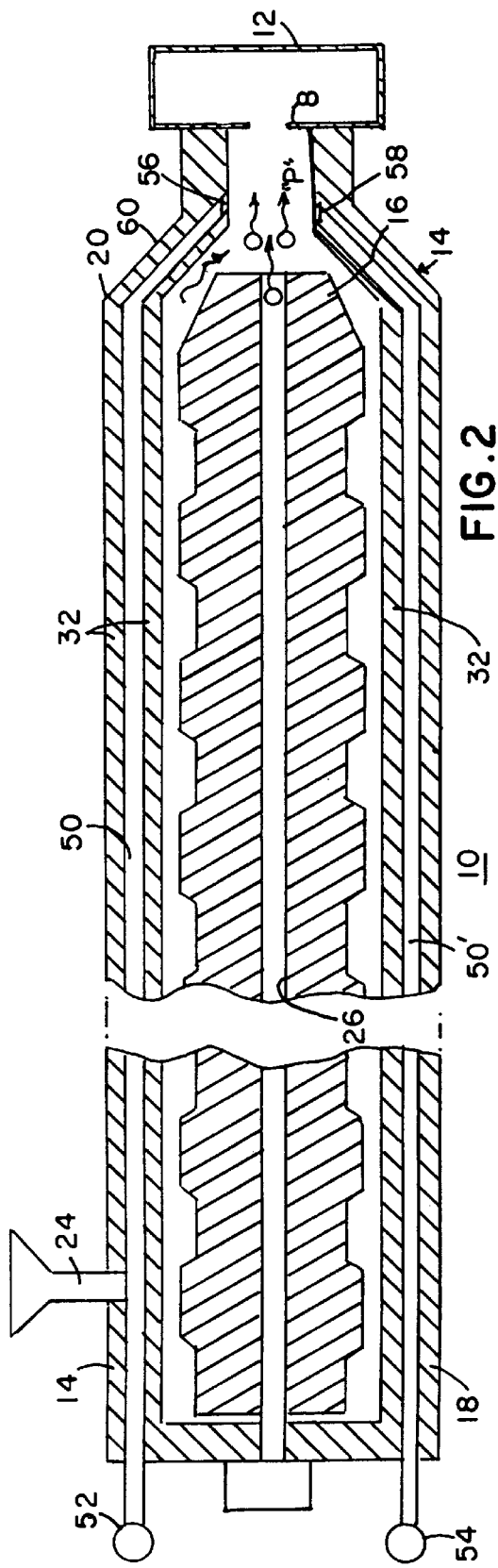
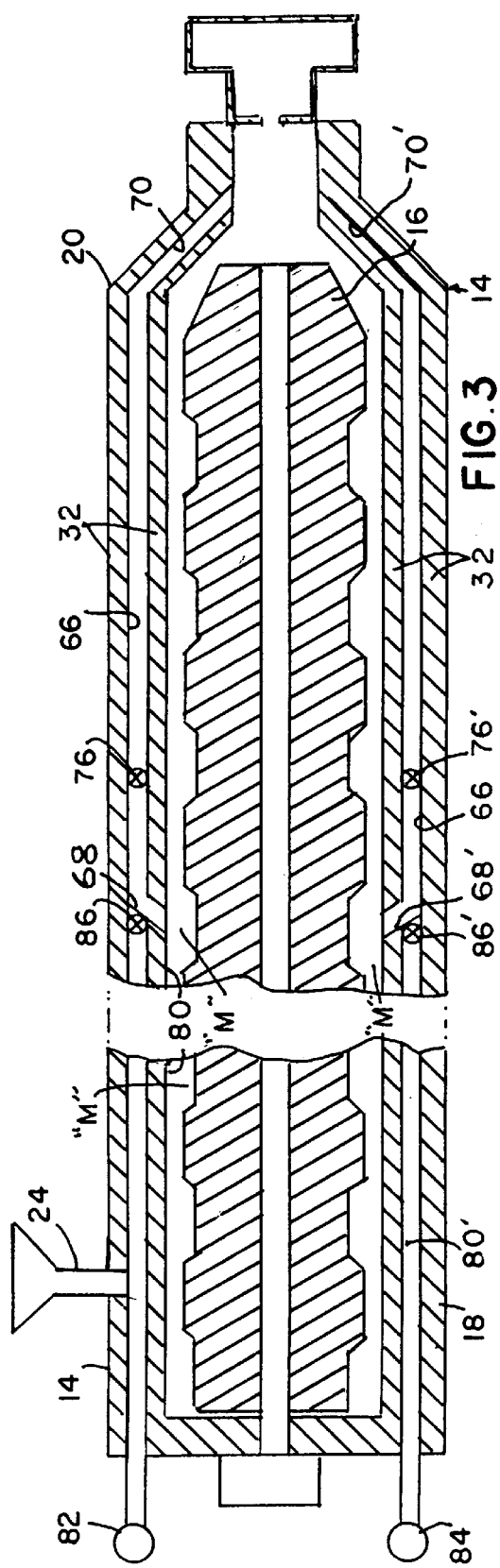

4,074,578

BARREL WALL CONDUIT ARRANGEMENTS FOR A PLASTIC PROCESSING SCREW MACHINE

RELATED APPLICATIONS

This is a Continuation-In-Part application of U.S. application Ser. No. 08/511,055 filed Mar. 8, 1995, now U.S. Pat. No. 5,670,112, which is a Contiuation-In-Part application of Ser. No. 08/393,200, filed Feb. 23, 1995, now abandoned, all of which are incorporated herein by reference.

BACKGROUND OF THE INVENTION

1. Field of the Invention

This invention relates to plastic processing machines, and more particularly to conduit arrangements the walls of barrel housings disposed about screw shafts utilized in extrusion and injection molding of plastics.

2. Prior Art

Injection molding and extrusion employs the steps of hot working a plasticized or melted thermoplastic material and forcing same under high pressure into a mold or mold space, then allowing the material to cool sufficiently so that it hardens to the extent that it can retain its shape after removal from the mold or as it emanates from the mold.

During the plasticating process, it is often desirable to add a further processed material with the plastic material being worked within a screw housing. It is further desired to be able to add a solid, such as a pellet, wire, gas or a vapor, into the actual plastic material being molded or extruded.

Limitations of present plasticating screw machinery prevent the simultaneous introduction of a gas and/or a liquid, and or a vapor, and/or a solid, into that thermoplastic material as it is going into a mold or die, along with the simultaneous temperature control of any such medium treating that thermoplastic material.

It is therefore an object of the present invention, to provide a plasticating screw machine having capabilities not found in the prior art.

It is a further object of the present invention, to provide a screw machine which is able to present a solid and/or a liquid, and/or a vapor, and/or a gas, with barrel housing conduits dividing any flow paths of a plastic being molded and/or extruded.

It is yet a further object of the present invention, to provide an arrangement of conduits which permits the rapid treating, cooling and completion of a plastic part in a manner not found in the prior art.

It is yet still a further object of the present invention, to provide an extrusion and/or injection molding screw with multiple capabilities to mix and/or extrude and/or mold multiple components therewith in a manner not found in the prior art.

BRIEF SUMMARY OF THE INVENTION

The present invention relates to a plasticating screw machine for treating thermoplastic material and pressurizably directing that thermoplastic material into an extrusion die or into an injection mold.

The plasticating screw machine of the present invention comprises an external barrel shaped housing having an elongated Archimedian type screw shaft rotatively supported therewithin. The housing and the screw shaft have a proximal or first end and a distal or second end. The screw shaft is rotatively empowered at the proximal first end of the housing by a motor drive means thereattached. At least one material in-feed supply hopper may be arranged through the housing near the proximal end thereof.

The screw shaft may have a bore extending completely therethrough along its longitudinal axis, from its proximalmost end to its distalmost end.

A plurality of conduits may arranged within the wall of barrel housing surrounding the screw shaft, the barrel of such plasticating machines typically being at least about 2 to 3 inches thick. The conduits in one embodiment preferably extend longitudinally within the barrel wall, from the proximal end thereof, through to the distal end of the barrel wall and back again in a sinusoidal manner, the conduits acting as heat transfer ducts, to controllably effect the temperature of the plasticating machine and/or the material being worked between the rotatable screw shaft and the inside surface of the barrel housing. Those conduits may be in communication with a regulated heat source or a regulated refrigerant source, to heat or cool the barrel walls and/or material being worked therewithin.

In a further preferred embodiment of the present invention, the axial conduits spaced around the thick barrel housing walls about the screw shaft may be arranged so as to present the delivery of any combination of medium(s) such as fluids, gas, vapors, and or solids such as wires, reinforcement fibers, optical glass and/or plastic at or downstream of the plasticating screw and/or within the plastic being processed during the plasticating operation. Such medium(s) may permit the cooling, reinforcement, electrifying, lighting, softening, hardening, gasifying, hollowing or densification of any plastic being extruded or injected from the plasticating screw machine. This further embodiment comprises a plurality of medium sources arranged at the upstream or proximal end of the plasticating machine. Those medium sources are in communication with their respective conduits within the walls of the barrel housing. Those conduits have discharge orifices such as nozzles, jeweled or the like, directed into the housing wall adjacent the distal end of the screw shaft adjacent a mold in which the worked plastic is entering.

A yet further preferred embodiment of the present invention contemplates a plurality of shunt conduits spaced longitudinally within the wall of the barrel housing, the conduits having an upstream end arranged an a non-axially directed channel open to the annular mixing path between the outer surface of the screw shaft and the inner side of the wall of the barrel housing. The conduits within the wall of the barrel housing have a downstream end which open back into the flow path between the outer surface of the screw shaft and the inside wall of the barrel housing (the primary flow path). The movement or transfer of solid, melted or fluid material along outer path within the wall of the barrel housing provides yet a further controlled mixing arrangement to supply the downstream or distal end of the screw shaft in the housing enclosing and supporting the elongated screw shaft. An arrangement of valves may be disposed within the conduits in the barrel wall to regulate the amount of flow being diverted from the primary flow path to the outer shunt conduits, to change the amount of plasticating being performed upon the material going through the machine.

It is still yet a further embodiment of the present invention to provide a combination of axially disposed conduits having an upstream supply end at the proximal end of the machine, which conduits are controllably dischargable by valves feeding into the shunt conduits, which shunt conduits have their pickup ends at the primary flow path at a location within the generally mid-portion of the barrel housing walls, to provide a further combination of controlled mixing of compounds and conditions.

Thus there has been shown, a unique barrel housing wall construction for an injection molding machine or a plastic extrusion machine, wherein that same thick barrel housing wall has a plurality of function transfer means included therewith. The separate conduits may be utilized individually or in combination, to continuously or sequentially add or withdraw a medium such as a vapor, a gas, a liquid, a foam, or a solid, into a plasticated material going into or through a die or a mold. The multiple conduits may be utilized to duct additional gas, or vapor, or foam or liquid, solid, or cooling material, through the barrel wall surrounding the elongated screw shaft and/or into the discharge end of the housing or with material picked up in the primary flow path to be discharged at the downstream end of the machine into a mold or the like.

The invention thus comprises a plasticating machine for the working and forcing of plastic material into a mold, the machine including an elongated housing having a first or proximal end and a second or distal end, an elongated screw shaft with a screw flight therearound, the screw shaft being rotatably supported in the elongated housing, for the working of plastic between the screw shaft and the elongated barrel housing, and at least one delivery conduit generally longitudinally arranged within the thick barrel housing wall, from a proximal end to a distal tip end thereof, to permit delivery of a medium longitudinally within the barrel wall and discharged into any plastic being driven from the machine. The medium may be any single or combination of components selected from the group comprising vapor, liquid, gas, powder or solid.

The delivery conduit(s) in the barrel wall each may have a time and quantity controlled supply duct arranged on its proximal end, to supply the medium to the conduit for distribution of the medium into any plastic being delivered to a mold adjacent the distal end of the screw shaft. At least one of the conduits in the barrel wall may be arranged to carry a vacuum, to return a medium from the distal end of the screw shaft to the proximal end thereof. At least one of the conduits may be arranged to carry a cooling fluid therethrough, so as to provide a temperature control to any medium traveling thereadjacent. The mold may comprise a hollow injection mold.

The invention also comprises a method of supplying a plastic to a mold for the manufacture of a plastic part therefrom, including the steps of providing an elongated rotatable screw shaft within an elongated barrel housing, the housing having a mold adjacent a distal end thereof, at least one delivery conduit longitudinally within the barrel wall, so as to permit a medium to be directed within the wall conduit(s) to any plastic being delivered to the mold adjacent the distal end of the housing. The method may include the step of providing a plastic material pickup at the primary flow path for the delivery conduit longitudinally disposed within the barrel wall, to permit controlled delivery of any medium with respect to the mold thereadjacent. The method may include the step of arranging a plurality of conduits within the wall of the barrel housing, to permit the delivery of a plurality of mediums therethrough, to allow any plastic driven from the housing to be mixed with and/or treated by the mediums. The method may include the step of supplying any medium to the proximal end of the axial conduits, and/or the shunt conduits, the mediums being selected from the group comprising: a vapor, a cooling gas, a heated gas, a liquid, an optical fiber, a reinforcing fiber, an electrical conductor, and electrical resistor.

BRIEF DESCRIPTION OF THE DRAWINGS

The objects and advantages of the present invention, will become more apparent, when viewed in conjunction with the following drawings, in which:

FIG. 2 is a view similar to that of FIG. 1, showing a further embodiment of the present invention; and FIG. 3 is a view similar to that of FIG. 1, showing a still further embodiment of the present invention.

DESCRIPTION OF THE PREFERRED EMBODIMENTS

Figure 1:
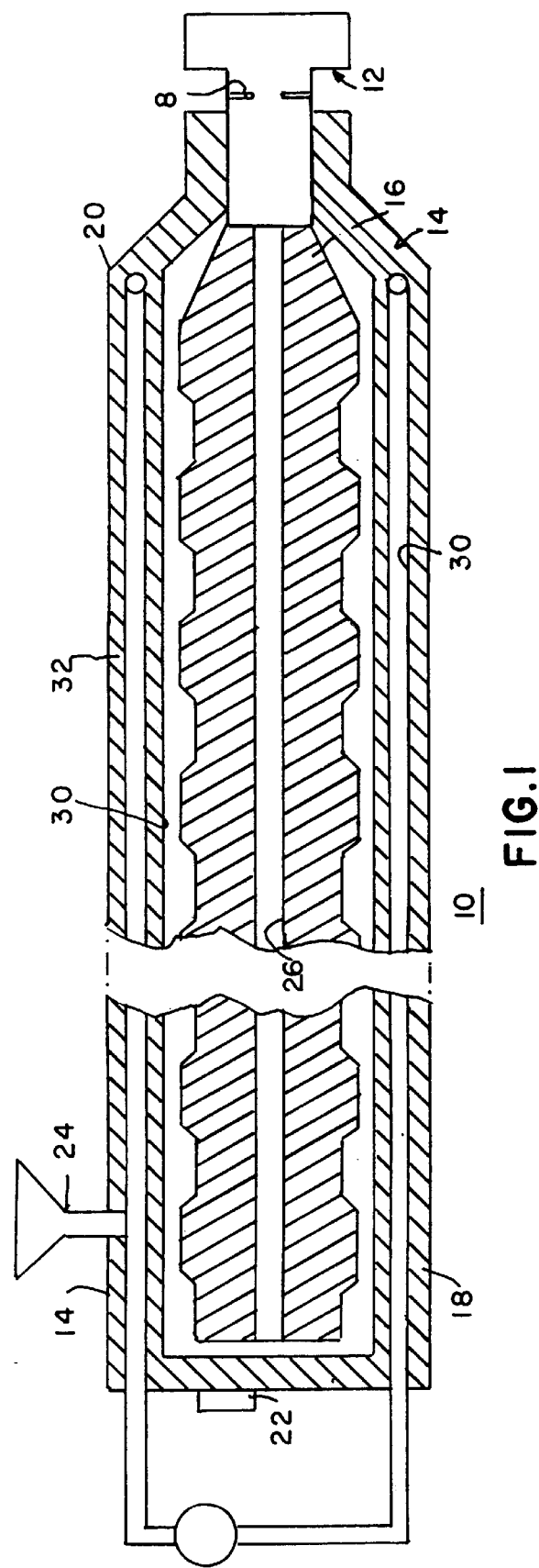
FIG. 1 is a side elevational view of a machine for working plastic, shown in section, having a plasticating screw shaft supported within a barrel housing, the barrel housing having a multiple conduit assembly therewithin for treatment of thermoplastic material within the machine, constructed according to the principles of the present invention.

Referring now to the drawings in detail, and particularly to FIG. 1, there is shown the present invention which relates to a plasticating screw machine 10 for treating of thermoplastic material and pressurizably directing that thermoplastic material into an extrusion die 8 or into an injection mold 12 thereadjacent, shown together for convenience.

The plasticating screw machine 10 of the present invention comprises an external barrel shaped housing 14 having an elongated screw shaft 16 rotatively supported therewithin. The housing 14 and the screw shaft 16 have a proximal or first end 18 and a distal or a second end 20. The screw shaft 16 is rotatively empowered at the proximal first end 18 of the housing 14 by a motor drive means 22 thereattached. At least one material in-feed supply hopper 24 may be arranged through the housing 14 near the proximal end 18 thereof.

The screw shaft 16 may have a bore 26 extending completely therethrough along its longitudinal axis, from its proximalmost end to its distalmost end. A plurality of conduits 30 may arranged within the wall 32 of barrel housing 14 surrounding the screw shaft 16, the barrels of such plasticating machines typically being at least about 2 to 3 inches thick. The conduits 30 in one embodiment preferably extend longitudinally within the barrel wall 32, from the proximal end 18 thereof, through to the distal end 20 of the barrel wall 32 and back again in a sinusoidal manner, the conduits acting as heat transfer ducts, to controllably effect the temperature of the plasticating machine and/or the material being worked between the rotatable screw shaft and the inside surface of the barrel housing. Those conduits may be in communication with a regulated heat source/pump or a regulated refrigerant source/pump 44, to heat or cool the barrel wall 32 and/or material being worked between the screw 16 and the inside surface of the barrel wall 32.

In a further preferred embodiment of the present invention, as shown in FIG. 2, a plurality of axial conduits 50 and 50' are shown spaced around the thick barrel housing walls 32 about the screw shaft 16, and may be arranged so as to present the delivery of any combination of medium(s) such as fluids, gas, vapors, and or solids such as wires, reinforcement fibers, optical glass and/or plastic at or downstream of the plasticating screw and/or within the plastic being processed during the plasticating operation. Such medium(s) may permit the cooling, reinforcement, electrifying, lighting, softening, hardening, gasifying, hollowing or densification of any plastic being extruded or injected from the plasticating screw machine 10. This further embodiment, as shown in FIG. 2, comprises a plurality of medium sources 52 and 54, arranged at the upstream or proximal end 18 of the plasticating machine 10. Those medium sources 52 and 54 are in communication with their respective conduits 50 and 50' within the walls 32 of the barrel housing 14. Those conduits 50 and 50' may each have a discharge orifice 56 and 58, such as nozzles, jeweled or the like, directed through the housing wall 60 adjacent the distal end of the screw shaft 16 and into the plastic flow path adjacent the mold 8 or 12, in which the worked plastic "P" or medium, is entering.

A yet further preferred embodiment of the present invention, as shown in FIG. 3, contemplates a plurality of shunt conduits 66 and 66', spaced longitudinally and annularly within the wall 32 of the barrel housing 14, the shunt conduits 66 and 66' having an upstream end 68 and 68' arranged an a non-axially directed channel open to the annular mixing path "M", between the outer surface of the screw shaft 16 and the inner side of the wall 32 of the barrel housing 14. The conduits 68 and 68' within the wall 32 of the barrel housing 14, may open back into the flow path "M" between the outer surface of the screw shaft 16 and the inside of the wall 32 of the barrel housing 14 (the primary flow path), at any location downstream of the screw shaft 16, as shown by end channels 70 and 70' within the distal end 20 of the housing 14, opening and discharging adjacent the entry of the mold 8 or 12. The movement or transfer of melted or fluid material along an outer path 66 and 66' within the wall 32 of the barrel housing 14 provides yet a further controlled mixing arrangement to supply the downstream or distal end of the screw shaft 16 in the housing 14 enclosing and supporting the elongated screw shaft 16. An arrangement of controlled valves 76 and 76' may be disposed within the conduits 66 and 66' in the barrel wall 32 to regulate the amount of flow being diverted from the primary flow path "M" to the outer shunt conduits 66 and 66', to change the amount of plasticating being performed upon the material going through the machine.

It is still yet a further embodiment of the present invention to provide a combination of axially disposed conduits 80 and 80', as shown in FIG. 3, which conduits 80 and 80' have an upstream supply source 82 and 84 at the proximal end 18 of the machine 10, which conduits 80 and 80' are controllably dischargable by regulated valves 86 and 86' feeding into the shunt conduits 66 and 66', which shunt conduits 66 and 66' have their pickup ends 68 and 68' angled towards the primary flow path "M" at a location within a generally axial mid-point of the barrel housing walls 32, to provide a further combination of controlled mixing of compounds, conditions.

Thus there has been shown, a unique barrel housing wall construction for an injection molding machine or a plastic extrusion machine, wherein that same thick barrel housing wall has a plurality of medium transfer means arranged therewithin. The separate conduits may be utilized individually or in combination, to continuously or sequentially add or withdraw a medium such as a vapor, a gas, a liquid, a foam, a solid, a partially worked plastic material, for discharge into a worked plasticated material going into or through a die or a mold. The multiple conduits may be utilized to duct additional gas, or vapor, or foam or liquid, solid, or cooling material, through the barrel wall surrounding the elongated screw shaft and/or into the discharge end of the housing or with material picked up in the primary flow path to be discharge at the downstream end of the machine into a mold or the like.

We claim:

1. A method of supplying a thermoplastic material for the manufacture, by a plasticating machine, of a plastic part therefrom, comprising the steps of:

providing an elongated rotatable screw shaft within an elongated barrel housing, said barrel housing having a proximal end and a distal end, a primary flow path for the plasticating of thermoplastic being defined between said screw shaft and said barrel housing;

arranging at least one delivery conduit disposed longitudinally within a wall of the barrel housing;

supplying a thermoplastic material to said primary flow path and rotating said screw shaft to plasticate said thermoplastic material;

directing a medium from a medium source through said delivery conduit; shunting at least a portion of said thermoplastic material from said primary flow path through a shunt conduit disposed longitudinally within said barrel wall, said delivery conduit extending from a location proximal to said shunt conduit and said shunt conduit extending from said delivery conduit to a location adjacent said distal end of said housing;

feeding said medium from said delivery conduit into said thermoplastic material in said shunt conduit; and deliverying said shunted thermoplastic material and said medium through said shunt conduit to a downstream location of said primary flow path for the manufacture of a part from said thermoplastic material.

2. The method of claim 1 including the step of:

arranging a plurality of delivery conduits within said wall of the barrel housing, to permit the delivery of a plurality of mediums therethrough, to allow said thermoplastic material to be mixed with and/or treated by said mediums.

3. The method of claim 2, including the step of:

said mediums being selected from the group consisting of: a vapor, a cooling gas, a heated gas, a liquid, an optical fiber, a reinforcing fiber, an electrical conductor, and electrical resistor.

* * * * *